United States Patent [19]
Dalton

[11] Patent Number: 4,857,053
[45] Date of Patent: Aug. 15, 1989

[54] MATRIX SEPTUM

[76] Inventor: Michael J. Dalton, 9432 Monticello Ave., Evanston, Ill. 60203

[21] Appl. No.: 238,042

[22] Filed: Aug. 29, 1988

[51] Int. Cl.⁴ .............................................. A61M 5/00
[52] U.S. Cl. ..................................... 604/93; 604/175; 604/244
[58] Field of Search ................... 604/93, 175, 87, 148, 604/200, 244; 428/258

[56] References Cited

U.S. PATENT DOCUMENTS

| | | |
|---|---|---|
| 3,310,051 | 3/1967 | Schulte . |
| 3,640,269 | 2/1972 | Delgado . |
| 3,971,376 | 7/1976 | Wichterle . |
| 4,190,040 | 2/1980 | Schulte . |
| 4,464,178 | 8/1984 | Dalton . |
| 4,490,137 | 12/1984 | Moukeibir .................. 604/175 |
| 4,543,088 | 9/1985 | Bootman et al. . |
| 4,673,394 | 6/1987 | Fenton et al. . |
| 4,692,146 | 9/1987 | Hilgir ............................ 604/175 |
| 4,710,167 | 12/1987 | Lazorthes . |
| 4,710,174 | 12/1987 | Moden et al. . |

*Primary Examiner*—Stephen C. Pellegrino
*Attorney, Agent, or Firm*—Richard L. Hansen

[57] ABSTRACT

A matrix septum material, especially useful in medical applications such as implantable drug delivery devices, is provided by retaining a penetrable, resilient, elastomer under compression between webs having peripheries which frame perforations to form individual, self-sealing cells in the matrix.

20 Claims, 2 Drawing Sheets

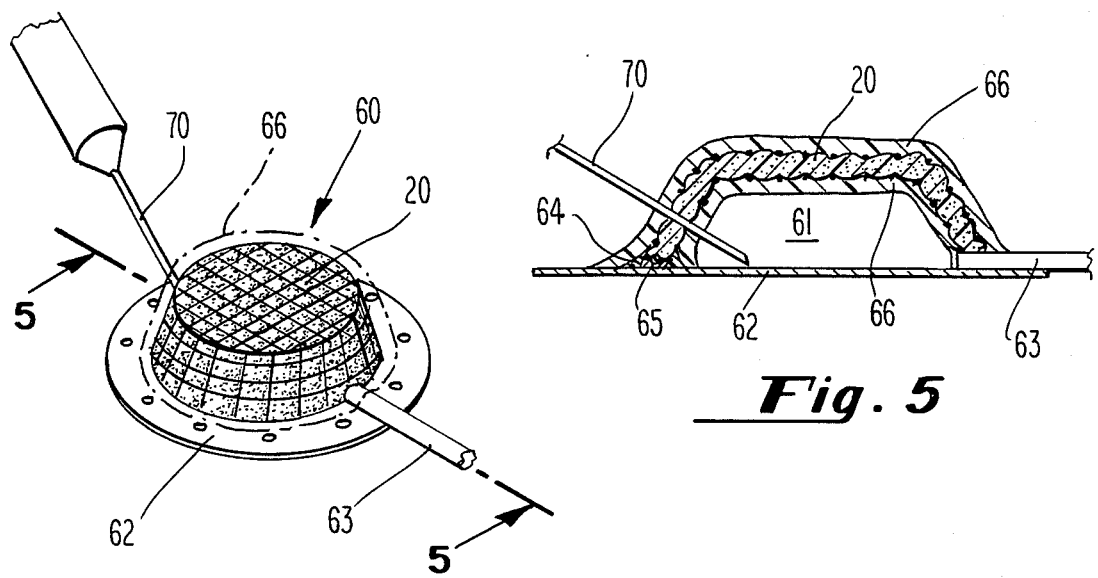
Fig. 4
Fig. 5
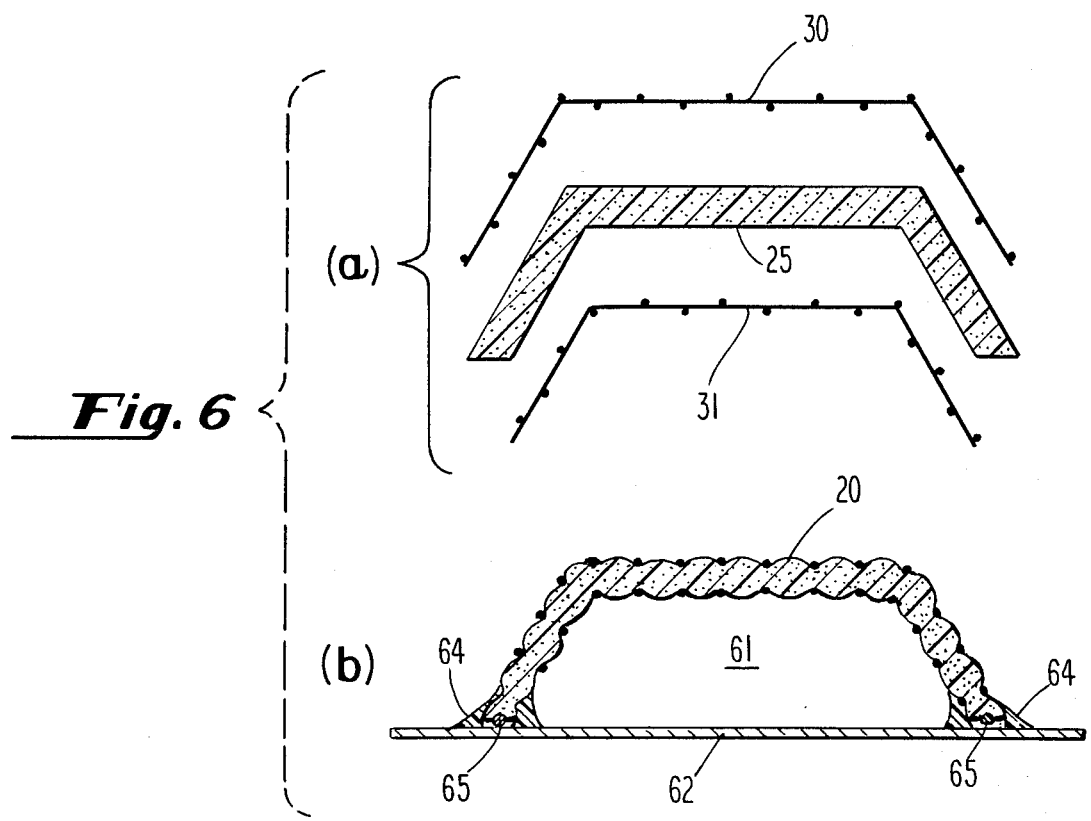
Fig. 6

MATRIX SEPTUM

This invention is in the field of puncturable, self-resealing septum closure mechanism for containers; more specifically, this invention relates to septums especially useful in medical applications, e.g., for sealing subcutaneously implanted drug delivery devices, particularly liquid delivery devices which are refillable via a hypodermic needle or conduit.

It is known in the art of drug therapy to implant a fluid delivery device beneath the skin, i.e., a penetrable receptacle, depot, port, hollow capsule or container. The receptacle is filled from time to time by hypodermic needle injection with a multidose quantity of a drug delivered through the wall of the receptacle or through a discrete penetrable area/septum which is part of the wall. The drug is then released slowly and continuously, e.g., via an outlet catheter or drug permeable membrane, to a site in the body requiring medication. Using this technique, the drug is supplied to the site relatively undiluted by body fluids, and the drug is more effective than when injected intramuscularly or into the blood stream. This technique is especially useful with certain cytotoxic drugs used in cancer chemotherapy and also has the advantage of decreasing the number of times the skin must be punctured, thereby reducing the risk of trauma and infection. The device also can be used to collect a body fluid, and the fluid can be withdrawn by needle.

One of the problems with implantable drug delivery devices is the tendency of the devices to develop leaks after being punctured. Sometimes a needle will remove a core of the septum material when the needle is removed, or the structural integrity of the septum material simply breaks down after multiple needle insertions. Regardless of the septum failure mechanism, it will be evident that drug leaks are unacceptable.

Various steps have been taken to construct a drug delivery port which can be punctured, but which reseals upon needle removal and does not leak after many punctures. Silicone rubber has been useful in this regard, and under the proper circumstances it can be punctured, but reseals itself.

Elastomeric materials, such as silicone rubber, have been employed as the penetrable wall material in several drug delivery ports described in the prior art. Such applications are reported in U.S. Pat. Nos. 3,310,051; 3,640,269; and 4,710,174, for example. However, it has been known for some time that walls so constructed tend to develop leaks, especially if the drug is added to the port under some pressure from the syringe or an external infusion pump. It is known that a pressure of 60–100 psi can be developed by an individual operator injecting liquid into a port using a 2 cc syringe. These pressures can easily deform, expand, and cause an unsupported silicone rubber depot to rupture. This problem has been enunciated in U.S. Pat. No. 4,190,040, for example.

In meeting this problem, various modifications have been made. For example, textile materials can be incorporated to strengthen the elastomeric wall material according to U.S. Pat. No. 3,971,376. Alternatively, a wall structure utilizing a silicone gel sandwiched between discrete silicone rubber sheets is disclosed in U.S. Pat. No. 4,190,040. The converse, a silicone rubber sheet coated with a flexible silicone layer is disclosed in U.S. Pat. No. 4,710,167. All of these modifications tend to restore or improve the elastomeric sealing quality of the wall inherent in the material of which it is constructed. However, in order to remain self-sealing, the wall must be relatively thick, which detracts from the flexibility and compliance of the drug depot, as well as the small size required in an implanted port. In addition, care must be taken to use only small diameter needles.

In another approach to the problem, it is disclosed in U.S. Pat. No. 4,543,088 that the interior of the drug chamber within the depot can be designed in such a way that fluid pressure within the chamber, tending to bulge it, creates compressive forces which seal needle punctures in the depot wall. However, the resultant depot has thick, heavy walls, producing patient discomfort.

In yet another attempt to solve the problem, a wall of the drug delivery depot may be provided with a discrete penetrable septum area within which all needle punctures are received. Discrete septums are generally incorporated into depots having otherwise hard, impenetrable walls. Such septums are described in U.S. Pat. Nos. 4,465,178 and 4,673,394. In these applications, an elastomeric septum, typically silicone rubber, is affixed to the depot in a physically compressed state, so that punctures are resealed, not only because the elastomer inherently tends to fill the void created as the needle is withdrawn, but also because of the external physical forces acting upon it. The depots which utilize discrete septums of this type are relatively noncompliant, leading to some patient discomfort, due in part to the bulky components required to retain the septum under the proper compressive forces. On the other hand, the discrete septums generally provide reliable self-sealing even though the drug is added to the depot under pressure, and there are few restrictions on the size needle that can be used.

Thus, it is the primary objective of this invention to overcome the various problems associated with the transfer of fluids to or from a penetrable, sealed container using a hollow conduit. Although the invention is of broad application to penetrable, sealed containers in general, it is especially directed to the problems associated with implanted drug delivery devices or conduits. Within this latter context, specific objectives include providing a new septum material which overcomes the structural weakness of unsupported silicone rubber and affords reliable resealing after multiple needle punctures, as reliable as a discrete septum under compression, but which does not simultaneously require that the device be rigid and noncompliant. Another objective is to provide a septum material which can be readily adapted and conformed to various desired sizes and shapes. Yet another objective is the provision of a drug delivery device which includes a large septum area, penetrable from many angles, but which retains the reseal reliability and structural integrity of septums maintained under compression, even when subjected to high internal fluid pressures.

These objectives, and others not explicitly stated, are attained in a novel material, one embodiment of which is a sheet-like consruction which incorporates both the flexibility and conformability of a relatively thin, resilient elastomeric depot wall with the reliable resealing associated with a discrete elastomeric septum under compression. Other embodiments of the novel material include various shaped articles, including drug delivery devices, such as receptacles, ports and depots. The new material is referred to herein as a "matrix" or "compound" septum, and the construction includes (1) at least one penetrable, resilient, elastomeric layer having front and back faces; (2) a plurality of webs having peripheries framing perforations, each web being in contact with at least one layer face; together with (3) means for urging the webs toward each other, thereby compressing the layer without substantially obstructing the perforations.

Thus, the septum of this invention, viewed face-on, resembles a matrix of lines or the compound eye of an insect, each perforation of the web framing an individual, penetrable, self-sealing cell in the matrix or compound septum. Each cell of the resilient layer, under compression from its framing web periphery, functions as an individual septum, the resealing characteristics of which are taught in U.S. Pat. No. 4,464,178.

The features of the new matrix septum, as well as the manner of making it and using it, will be clarified by reference to the drawings which accompany this specification and to the detailed description which follows.

In the drawings:

FIG. 4 is a perspective view showing an implantable drug delivery device which includes a matrix septum material of this invention.

FIG. 5 is a cross-sectional view taken along lines 5—5 in FIG. 4.

FIG. 6 illustrates a method by which the matrix septum material for the drug delivery device of FIG. 4 is made.

Figure 1:
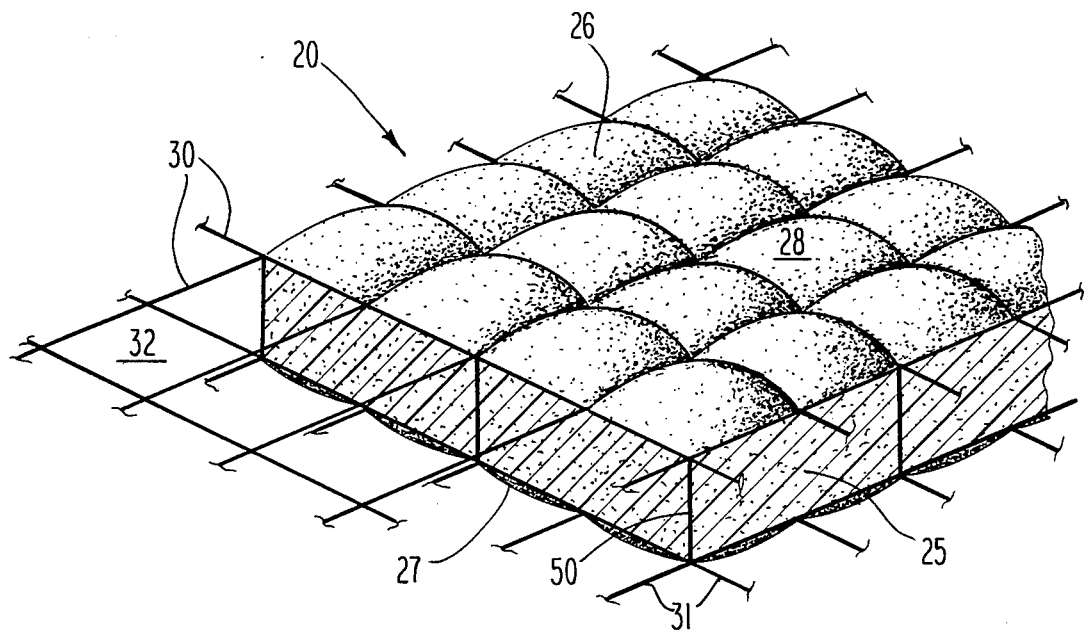
FIG. 1 is a diagrammatic perspective view of one portion of a matrix septum material of this invention embodied in a sheet-like construction.
Figure 2:
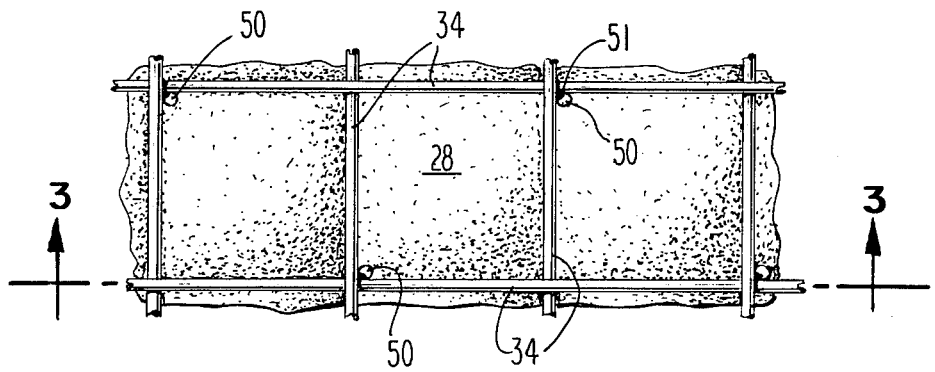
FIG. 2 is a top view of the septum material shown in FIG. 1.
Figure 3:
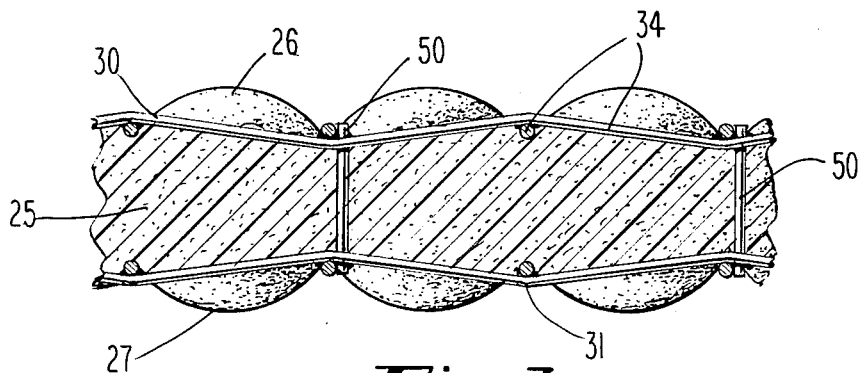
FIG. 3 is a cross-sectional view taken along lines 3—3 in FIG. 2.

Referring now primarily to FIGS. 1-3, matrix or compound septum material 20 includes resilient, elastomeric, needle penetrable layer 25, which is contacted on front face 26 by web 30 and on back face 27 by web 31. Means 50 are also provided for urging webs 30 and 31 toward each other, compressing layer 25, producing a multi-septum matrix or compound septum. The perforations 32 framed by the web periphery 34 create individual, penetrable, self-sealing cells in the compound system.

With regard to layer 25, a number of materials are of potential use, depending upon the application. Layer 25 must be a solid, i.e., it cannot spontaneously flow, and it must exhibit reasonable tensile strength and elongation and be capable of compression without permanent deformation under the force applied to compress it. Natural and synthetic rubbers, including butadiene polymers and copolymers, neoprene, chloroprene, and the equivalents thereof, are all potentially useful where the matrix septum material will be employed in general closure applications. Such applications include the closure of containers containing sterile materials, biologically dangerous agents, pyrophoric chemicals, hygroscopic reagents, etc., which are liquid and are sampled from time to time using a needle and syringe.

In medical applications, however, the choice of materials for layer 25 is more limited, since the material must be medically acceptable for the specific application. In the case of implantable devices, silicone rubbers have won acceptance for use in drug delivery ports. Thus, layer 25 may be constructed of suitable silicone rubbers, many of which are available commercially, e.g., from Dow Corning Corporation, Midland, Mich., but other medically acceptable elastomeric materials may also be employed. For most infusion port applications the matrix septum of this invention preferably incorporates a relatively soft silicone rubber, e.g., about 30–60 Shore A. This silicone rubber is to be distinguished from the silicone gel described in U.S. Pat. No. 4,190,040, such gels being much softer in general and exhibiting near zero tensile strength and elongation. Layer 25 may be reinforced internally with an embedded, woven polyester fabric or other fabric or screen, e.g., titanium screen.

The thickness of layer 25 will be tailored to the specific application. In many infusion device applications layer 25 will be in the range 0.08–0.3 inch thick, e.g., 0.125 inch thick.

Webs 30 and 31 can each be made of the same material or different materials, and the perforations 32 may or may not be of the same size or shape. In addition, it is not necessary that the perforations in the webs be in register. However, ease of fabrication is enhanced if the webs have the same type of perforations and they are in register as shown in FIGS. 1-3.

Dependent upon the web material, the flexibility inherent in layer 25 may or may not be retained in the matrix septum. Webs 30 and 31 may be made of loosely woven natural or synthetic, including fibrous polymeric, organic or inorganic fabric, especially fabric made with thread which is relatively inelastic. In medical applications, for example, fabric made of polyester thread is satisfactory, as are fabrics made from suture materials, such as silk, but other fibers such as graphite or glass may also be used. The thread denier and composition are selected so that the web will undergo little or no stretching under the compressive force applied to layer 25.

Another type of web material which may be used is metal wire screen. Such wire screen may be made of any suitable medically acceptable metal, such as titanium or stainless steel, for example. Standard grade type 316L stainless steel wire cloth, which is available commercially, can be employed with good results. Although such screen in various weave patterns can be used, basketweave screen is very satisfactory.

The aforesaid types of webs, which are especially useful to make sheet-like embodiments of the matrix septum materials, may also be used to produce various three-dimensional shaped articles. Such articles can be producted, e.g., by bending, folding or draping a preformed sheet-like matrix septum and fastening it in place. Alternatively, such articles can be produced by employing at least a nest pair of webs, which may be made of wire, for example, and which reflect the desired shape, and inserting the elastomeric layer between them. In any event, means are also provided for urging the webs together, toward each other, in order to compress the elastomeric layer between them.

The perforation size in webs may vary in the same way, whether made of fabric or screen, or whether the matrix septum is sheet-like or an arbitrary three-dimensional shape, depending upon specific details of the application. The larger the perforation area, the thicker and/or softer the elastomeric layer should be, and/or the greater the force urging the webs toward each other. Thread or wire mesh with about 6–14 perforations per inch and thread or wire diameters in the range of about 0.015–0.065 inch is satisfactory. With these mesh and web sizes, the perforations generally range from about 0.040 to about 0.132 inch in length and width, although the length and width of the perforations can differ if desired, and the perforations need not be square, but they can be rectangular, triangular, hexagonal, circular, planar, curved, etc. The size of the perforations will, of course, be selected to pass the desired size needle or conduit. Furthermore, there is no upper limit to the number of perforations a matrix septum of this invention may contain, the number only being limited by the physical size of the construction it is possible to handle. As to the lower limit, it is only necessary that a matrix septum of this invention carry at least one perforation.

In addition to the possibility that one or both of the webs can be made of fabric, screen, or wire, it is also possible to construct either web of acceptable perforated metal or plastic sheet. However, these materials in general are less desirable, since the flat surfaces between perforations act to impede transit of a needle. On the other hand, threads or wires having round cross sections tend to deflect a needle which strikes them.

Webs made of fabric are more likely to lead to a matrix septum which is very flexible than would the use of perforated plate webs. Wire or wire screen webs can lead to relatively flexible or rigid matrix septums depending upon the type and size of the wire. In general, it is preferred that the areas of faces 26 and 27 which are perforations as 32 be greater than the areas which are web peripheries as 34.

A number of means may be employed to force webs 30 and 31 toward each other, compressing layer 25. For example, webs 30 and 31, in contact with the faces of layer 25, can be forced toward each other mechanically, e.g., in a press, compressing layer 25 at periphery 34 of each cell 28. The amount of compression required will depend upon the nature of layer 25 and the size of the perforations 32 in the webs 30 and 31. For example, a silicone layer nominally 0.125 inch thick faced with webs of 0.020 in. diameter stainless steel basketweave wire having perforations about 0.150 in.×0.150 in. is compressed to about 0.080 in. at the periphery of each cell, while the central portion of each cell is about 0.150 in. thick.

With layer 25 forced into a compressed state, any of several different means may be employed for maintaining the compression and urging the webs toward each other, but without substantially obstructing the perforations. For example, if the web is relatively stiff, e.g., wire screen, only the outer edges of the webs need be welded or otherwise adhered together. In another method, the webs can be sewn together through layer 25 at the number of points sufficient to maintain the desired compression; in that case, thread such as about 0.010 in. diameter stainless steel or nickel/brass wire can be employed, but polyester, silk or other natural or synthetic polymeric thread materials can also be used. Such sewing, pulling the stitches uniformly tight, can also suffice to urge the webs agaisnt layer 25 in the absence of external force applied to compress the construction. Alternatively, rods 50 can be passed through layer 25 and affixed to webs 30 and 31 by welding or adhesive bond 51; for example, stainless steel rods in the range of about 0.010 in. to about 0.025 in. in diameter can be used as shown in FIGS. 1–3. In addition, it may be desirable to sew, wire, weld, glue, or otherwise attach webs 30 and 31 together circumferentially along the edge of the matrix septum, as mentioned above.

Although the matrix septum material illustrated in FIGS. 1–3 includes a single elastomeric layer and a pair of webs, each in contact with one face of the single layer, the requirements of some resealable closures may demand that more than one elastomeric layer be employed, i.e., that the layers be stacked. In this event it may be desirable to contact, not only each exposed face, but also unexposed faces of the stacked layers, with one or more webs between the layers. That is, it may be desirable to employ a plurality of webs, each web being in contact with at least one layer face: e.g., webs between layers may be in contact with two faces. Furthermore, in certain applications, e.g., applications in which the turbulence or pattern of fluid flow across the matrix septum is critical, it may be desirable to embed the matrix septum, i.e., one or both sides, with a coating which smooths the surface. In this regard, a silicone potting resin or curable coating may be employed.

In addition to the matrix or compound septum material described above, which is of general use in sealing applications, this invention includes implantable drug delivery devices which include the matrix septum material. A drug delivery port of this invention is shown in FIGS. 4 and 5. Although drug delivery devices of this invention can take many shapes and forms because of the versatility of matrix septum material 20, a drug delivery port 60, in which drug reservoir 61 is shaped like a truncated cone, is a desirable shape. Drug reservoir 61 is enclosed by matrix septum 20 and suture flange 62, drug outlet catheter 63 being provided to perform its usual function. Matrix septum 20 is coated with silicone layer 66. It will be noted the incorporation of matrix septum 20 permits needle 70 to access the drug reservoir from almost any angle and with confidence that the puncture will be reliably sealed when the needle is withdrawn.

The matrix septum material of this invention can be incorporated into a drug delivery device or other arbitary three-dimensional article in a number of different ways. One of these ways is illustrated in FIG. 6. Preformed webs 30 and 31, desirably made of metal wire and sized to nest in contact with elastomeric layer 25, are forced together, compressing layer 25. The webs are urged toward each other after the force is removed by welding the edges together along wire 65, which is led circumferentially about the septum terminus. The septum terminus is affixed to and against flange 62 with adhesive/potting resin 64. Alternatively, the matrix septum material in sheet form can be affixed to a truncated cone framework by sewing, etc. and reservoir 61 created by attaching the framework to suture flange 62.

EXAMPLE 1

A circular piece of 0.125 in. thick silicone rubber made from Dow Corning SILASTIC MDX-4-4210 Medical Grade Elastomer was compressed using pliers to about 0.060 in. between two stainless steel, basket weave screens made from wire 0.028 in. in diameter and having 0.097 in. square perforations. While compressed, the screens were secured together at about every other steel wire intersection using 0.009 in. diameter nickel/brass wires passed through the silicone rubber, around the steel wire intersections on either side of the silicone layer, and tied with square knots. The resultant matrix septum material was formed into a dome, which was affixed to a rigid plastic base to form an enclosed receptacle. A catheter-like outlet tube was led into the receptacle, and the entire port was then potted in a thin layer of the MDX-4-4210 silicone rubber. The receptacle was pressurized via the outlet tube with air at 10 psi, and the port was immersed in water; no air leaks were observed.

The receptacle was then punctured under water through the same 0.097 in. × 0.097 in. perforation 20 times with a 19 gauge Huber point needle. The port was tested with air at 10 psi after each puncture and was found to not leak.

A device of the aforesaid type was tested for failure under pressure by applying air at various increasing pressures to the receptacle through the outlet tube; the device withstood 84 psi before a leak developed.

EXAMPLE 2

Silicone rubber sheet, 0.125 in. thick and the same as that employed in Example 1, was formed into a dome-shaped receptacle. The receptacle was affixed to a rigid plastic base, and an outlet tube was led into the receptacle. The entire port was then potted in a thin layer of the same silicone rubber. As in Example 1, the receptacle was pressurized via the tube with air at 10 psi, and the port was immersed in water. No leaks were observed, but after a single puncture of the receptacle with a 19 gauge Huber point needle, the receptacle would not retain air at 10 psi.

A device of the same type swelled markedly under the application of increasing air pressure and ruptured at 12 psi.

EXAMPLE 3

A construction consisting of silicone gel, 0.120 in. thick (Dow Corning Q7-2167/Q7-2168 in 3:1 ratio), was sandwiched between 0.040 in. thick sheets of Dow Corning SILASTIC MDX-4-4210 Medical Grade Elastomer cured in place. The construction was formed into a dome-shaped receptacle and affixed to a rigid base; an outlet tube was provided from the enclosed receptacle. As in Examples 1 and 2, the device was tested with air at 10 psi and found not to leak. When punctured under water with a 19 gauge Huber point needle, water followed the needle into the gel space and, when the needle was withdrawn, air from the receptacle followed the needle into the gel space. After two needle punctures the device would not retain air at 10 psi.

A device of the same type ruptured at 22 psi when subjected to increasing air pressures.

It will be evident that a number of variations in both the septum material pe se and in implantable drug delivery devices incorporating the septum material can be made while remaining within the spirit and scope of this invention. It will be appreciated, therefore, that the scope of the invention is broader than the specific embodiments set forth herein to illustrate it.

What is claimed is:

1. A matrix septum material which comprises
at least one penetrable, resilient, elastomeric layer having front and back faces;
a plurality of webs having perforations with peripheries, each web in contact with at least one layer face; together with
means for urging said webs toward each other, compressing said layer without substantially obstructing said perforations;
whereby each perforation frames an individual penetrable, self-sealing cell in the matrix septum.

2. The septum material of claim 1 wherein said layer is an elastomer selected from butadiene polymers an copolymers, neoprene, chloroprene, or silicone rubbers.

3. The septum material of claim 2 wherein said layer is silicone rubber.

4. The septum material of claim 1 wherein said webs are constructed from fabric, screen, wire or perforated plate.

5. The septum material of claim 1 wherein said perforations exceed said peripheries in area.

6. The septum material of claim 1 wherein said webs are urged toward each other by joining said webs with rods or stitches through said layer.

7. The septum material of claim 1 further comprising one layer and a pair of webs.

8. In an implantable drug-delivery device of the type to which a drug is added with a needle through a septum, the improvement therein which comprises including in the device a needle-penetrable, self-sealing matrix septum which includes
at least one penetrable, resilient, elastomeric, medically acceptable layer having front and back faces;
a plurality of webs having perforations with peripheries, each web in contact with at least one layer face; together with
means for urging said webs toward each other, thereby compressing said layer without substantially obstructing said perforations;
whereby each perforation frames an individual penetrable, selfsealing cell in the matrix septum.

9. The drug delivery device of claim 8 wherein said layer is an elastomer selected from butadiene polymers and copolymers, neoprene, chloroprene, or silicone rubbers.

10. The drug delivery device of claim 9 wherein said layer is silicone rubber.

11. The drug delivery device of claim 8 wherein said webs are constructed from fabric, screen, wire or perforated plate.

12. The drug delivery device of claim 8 wherein said perforations exceed said peripheries in area.

13. The drug delivery device of claim 8 wherein said webs are urged toward each other by joining said webs with rods or stitches through said layer.

14. The drug delivery device of claim 8 further comprising one layer and a pair of webs.

15. An implantable drug delivery device which comprises
a drug reservoir;
an outlet from said reservoir; and
a needle penetrable, self-sealing septum inlet into said reservoir, said septum comprising
at least one penetrable, resilient, elastomeric, medically acceptable layer having front and back faces;
a plurality of webs having perforations with peripheries, each web in contact with at least one layer face; together with
means for urging said webs toward each other, thereby compressing said layer without substantially obstructing said perforations.

16. The drug delivery device of claim 15 wherein said webs are urged toward each other by joining said webs together circumferentially.

17. The drug delivery device of claim 15 wherein said layer is silicone rubber.

18. The drug delivery device of claim 15 wherein said webs are constructed from fabric, screen, wire or perforated plate.

19. The drug delivery device of claim 15 wherein said perforations exceed said peripheries in area.

20. The drug delivery device of claim 15 further comprising one layer and a pair of webs.

* * * * *

UNITED STATES PATENT AND TRADEMARK OFFICE
CERTIFICATE OF CORRECTION

PATENT NO.    : 4,857,053
DATED         : August 15, 1989
INVENTOR(S)   : Michael J. Dalton It is certified that error appears in the above—identified patent and that said Letters Patent is hereby corrected as shown below:

In Col. 2, line 21 "4,465,178" should read --4,464,178--.
In Col. 2, line 60 "consruction" should read --construction--.
In Col. 3, lines 44-45 "system" should read --septum--.
In Col. 4, line 22 "Dependent" should read --Depending--.
In Col. 4, line 47 "producted" should read --produced--.
In Col. 4, line 50 "nest" should read --nesting--.
In Col. 5, line 26 "performations" should read --perforations--.
In Col. 5, line 56 "agaisnt" should read --against--.
In Col. 6, lines 54-55 "basket weave" should read --basketweave--.
In Col. 7, line 65 "an" should read --and--.
In Col. 8, line 25 "selfsealing" should read --self-sealing--.

Signed and Sealed this

Third Day of July, 1990

*Attest:*

HARRY F. MANBECK, JR.

*Attesting Officer*     *Commissioner of Patents and Trademarks*